United States Patent [19]
Kumar

[11] Patent Number: 5,891,368
[45] Date of Patent: Apr. 6, 1999

[54] FLUORANTHENOPYRANS

[75] Inventor: Anil Kumar, Pittsburgh, Pa.

[73] Assignee: PPG Industries, Inc., Pittsburgh, Pa.

[21] Appl. No.: 942,182

[22] Filed: Oct. 1, 1997

[51] Int. Cl.[6] .......................... G02B 5/23; C07D 311/78; C07D 305/00; C08J 5/15

[52] U.S. Cl. .................. 252/586; 524/84-87; 524/94-96; 524/100-104; 524/110; 544/132-141; 544/143-145; 544/146-147; 544/148-152; 544/153-154; 544/238-356; 544/366-369; 544/373-375; 548/311.4-364.4; 548/454-525; 549/213-331; 549/382

[58] Field of Search ..................... 549/382, 213, 549/331; 252/586; 544/375, 132, 141, 143, 145, 146, 147, 148, 152, 153, 154, 238, 358, 366, 369, 373; 524/10, 94, 84, 87, 96, 100, 104; 546/196; 548/311.4, 364.4, 454, 525

[56] References Cited

U.S. PATENT DOCUMENTS

| | | | |
|---|---|---|---|
| 3,361,706 | 1/1968 | Meriwether et al. | 260/39 |
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,360,653 | 11/1982 | Stevens et al. | 859/301 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/586 |
| 4,931,220 | 6/1990 | Haynes et al. | 252/586 |
| 4,994,208 | 2/1991 | McBain et al. | 252/586 |
| 5,066,818 | 11/1991 | Van Gemert et al. | 549/389 |
| 5,200,483 | 4/1993 | Selvig | 526/301 |
| 5,238,981 | 8/1993 | Knowles | 524/110 |
| 5,274,132 | 12/1993 | Van Gemert | 549/389 |
| 5,373,033 | 12/1994 | Toh et al. | 822/96 |
| 5,384,077 | 1/1995 | Knowles | 252/586 |
| 5,405,958 | 4/1995 | Van Gemert | 544/71 |
| 5,429,774 | 7/1995 | Kumar | 252/586 |
| 5,458,814 | 10/1995 | Kumar et al. | 252/586 |
| 5,466,398 | 11/1995 | Van Gemert et al. | 252/586 |
| 5,475,074 | 12/1995 | Matuoka et al. | 526/336 |
| 5,514,817 | 5/1996 | Knowles | 549/384 |
| 5,552,090 | 9/1996 | Van Gemert et al. | 252/586 |
| 5,552,091 | 9/1996 | Kumar | 252/586 |
| 5,565,147 | 10/1996 | Knowles et al. | 252/586 |
| 5,573,712 | 11/1996 | Kumar et al. | 252/586 |
| 5,578,252 | 11/1996 | Van Gemert et al. | 252/586 |
| 5,645,767 | 7/1997 | Van Gemert | 252/586 |
| 5,656,206 | 8/1997 | Knowles et al. | 252/586 |

OTHER PUBLICATIONS

Olah et al., *Friedel–Crafts and Related Reactions*, Interscience Publishers, Vol. 3, Chapter XXXI ("Aromatic Ketone Synthesis"), pp. 1–8, 1964.

Ishihara et al., "Regioselective Friedel–Crafts Acylation of 1,2,3,4–Tetrahydroquinoline and Related Nitrogen Heterocycles: Effect on NH Protective Groups and Ring Size", J. Chem. Soc. Perkins Trans. 1, 1992, pp. 3401–3406.

Sieglitz et al., "3–Hydroxyfluroanthene–1–,–2–, and –10–carboxylic acids", Chem. Abs., vol. 58, No. 7882b, 1963.

Bergmann et al., "Synthesis of Fluoranthene and its Derivatives", J. Amer. Chem. Soc., vol. 71, 1949, pp. 1917–1918.

Shenbor et al., "Preparation of 3–Fluoranthenol by the Action of Lead Tetraacetate on Fluoranthene", J. Org. Chem. of the USSR, vol. 5, 1969, pp. 140–141.

Sieglitz et al., "The Synthesis of Fluoranthene Derivatives from Monoethyl 4,4–(o,o'–Biphenylene) itaconate", Angew. Chem. internat. Edit., vol. 3, No. 8, 1964, p. 587.

Heller et al., Chem. Abstract vol. 102 No. 184,802, "Reactions of 4–fluoren–9–ylidene–2–methylpent–2–ene and 2–fluoren–9–yl–2–methylpentan–4–one" 1984.

Lee–Ruff Chem. Abstract Vol. 113 No. 152180, "Syntheses of fluoranthenol (1,2–b) thiophene and fluoranthen (3,2–b) thiophene, isosteres of benzofluoranthenes" 1990.

Shenbor et al., Chem. Abstract vol. 90 No. 151933, "Synthesis and Properties of 4–ethoxy–fluoranthenopyrylium & fluoranthenopyrone salts" 1979.

Shenbor et al., Chem. Abstract vol. 87 No. 166,977 "Absorption and luminescence of some fluoranthenooxazoles & 1–(9'–fluorantheno (',9'–d) oxazolyl)–2–arylethylenes",1977.

*Primary Examiner*—John Kight
*Assistant Examiner*—Raymond Covington
*Attorney, Agent, or Firm*—Irwin M. Stein; Frank P. Mallak

[57] ABSTRACT

Described are novel photochromic 8-substituted fluoranthenopyran compounds having certain substituents at the 5 position of the pyran ring. These compounds may be represented by the following graphic formula:

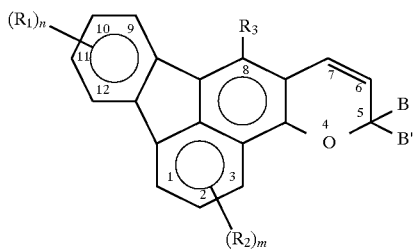

Also described are polymeric organic host materials that contain or that are coated with such compounds.

23 Claims, No Drawings

FLUORANTHENOPYRANS

DESCRIPTION OF THE INVENTION

The present invention relates to certain novel naphthopyran compounds. More particularly, this invention relates to novel photochromic 8-substituted fluoranthenopyran compounds and to compositions and articles containing such novel fluoranthenopyran compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion.

U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions. U.S. Pat. No. 5,645,767 describes novel photochromic indeno-fused 2H-naphtho[1,2-b]pyran compounds, the 2,1-positions of the indeno group being fused to the f side of the naphthopyran.

U.S. Pat. No. 5,458,814 discloses photochromic 2H-naphtho[1,2-b]pyran compounds having certain substituents at the number 5 and 6 carbon atoms of the naphtho portion of the naphthopyran, and at the 2-position of the pyran ring. These compounds have an acceptable fade rate in addition to a high activated intensity and a high coloration rate.

The present invention relates to novel 5H-fluorantheno [3,2-b]pyran compounds having certain substituents at the 5 position of the pyran ring. Certain other substituents are present at the number 8 carbon atom and yet other specific substituents may also be present at the number 1, 2, 3, 9, 10, 11 or 12 carbon atoms of the fluorantheno portion of the fluoranthenopyran ring. Photochromic compounds of the present invention include compounds that exhibit acceptable photochromic performance properties, such as activated intensity, coloraton rate and fade rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-à-vis, glass lenses. Moreover, photochromic transparencies for vehicles, such as cars and airplanes, have been of interest because of the potential safety features that such transparencies offer.

In accordance with the present invention, it has now been discovered that certain novel photochromic 5H-fluorantheno [3,2-b]pyrans may be prepared. These compounds may be described as fluoranthenopyrans having certain substituents at the number 8 carbon atom of the fluoranthenopyran ring and certain other substituents at the 5 position of the pyran ring. Other specific substituents may also be present at the number 1, 2, 3, 9, 10, 11 or 12 carbon atom of the fluorantheno portion of the fluoranthenopyran ring.

The foregoing described fluoranthenopyran compounds may be represented by the following graphic formula I in which the numbers 1 through 12 within the rings identify the ring atoms of the fluoranthenopyran:

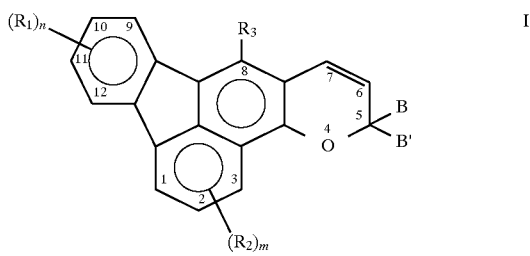

In graphic formula I, each $R_1$ and $R_2$ may be hydroxy, aryl, i.e., phenyl or naphthyl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy ($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di($C_1$–$C_6$)alkylaryl($C_1$–$C_6$)alkyl, mono- and di($C_1$–$C_6$)alkoxyaryl($C_1$–$C_6$)alkyl, mono- and di($C_1$–$C_6$) alkylaryl($C_1$–$C_6$)alkoxy, mono- and di($C_1$–$C_6$)alkoxyaryl ($C_1$–$C_6$)alkoxy, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, bromo, chloro and fluoro, and m and n are each the integers 0, 1 or 2. Preferably, each $R_1$ and $R_2$ are $C_1$–$C_4$ alkyl, $C_1$–$C_4$ alkoxy, chloro or fluoro, and m and n are each the integers 0 or 1. More preferably, each $R_1$ and $R_2$ are $C_1$–$C_3$ alkyl or $C_1$–$C_3$ alkoxy.

In graphic formula I, $R_3$ may be the group, —$CH_2$X or —C(O)W, X may be halogen, hydroxy, benzoyloxy, $C_1$–$C_6$ alkoxy, $C_2$–$C_6$ acyloxy, amino, $C_1$–$C_6$ mono-alkylamino, $C_1$–$C_6$ dialkylamino, i.e., di($C_1$–$C_6$)alkylamino, morpholino, piperidino, 1-indolinyl, pyrrolidyl, trimethylsilyloxy, or the group, —OCH($R_4$)Z; W may be the group, —OCH($R_4$)Z or an unsubstituted, mono-substituted, or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl; Z may be —CN, —CF$_3$, halogen, —C(O)R$_4$, or —COOR$_4$; R$_4$ may be hydrogen or C$_1$–C$_6$ alkyl; the heterocyclic ring substituents may be C$_1$–C$_6$ alkyl or C$_1$–C$_6$ alkoxy; or W may be —OR$_5$ or —N(R$_6$)R$_7$, wherein R$_5$ is hydrogen, allyl, C$_1$–C$_6$ alkyl, e.g., methyl, ethyl, propyl, butyl, pentyl, and hexyl, phenyl, mono(C$_1$–C$_6$)alkyl substituted phenyl, mono(C$_1$–C$_6$) alkoxy-substituted phenyl, phenyl(C$_1$–C$_3$)alkyl, mono (C$_1$–C$_6$)alkyl substituted phenyl(C$_1$–C$_3$)alkyl, mono (C$_1$–C$_6$)alkoxy substituted phenyl(C$_1$–C$_3$)alkyl, mono (C$_1$–C$_6$)alkoxy(C$_1$–C$_4$)alkyl, or C$_1$–C$_6$ haloalkyl; and R$_6$ and R$_7$ may each be selected from the group consisting of hydrogen, C$_1$–C$_6$ alkyl, C$_5$–C$_7$ cycloalkyl, phenyl and mono- or di-substituted phenyl; each of the phenyl substituents being C$_1$–C$_6$ alkyl or C$_1$–C$_6$ alkoxy; and each of the halogen or halo groups being fluoro or chloro.

Preferably, R$_3$ is the group, —CH$_2$X or —C(O)W, wherein X is hydroxy, C$_1$–C$_4$ alkoxy, or C$_2$–C$_4$ acyloxy, W is the group, —OCH(R$_4$)Z, or an unsubstituted or mono-substituted heterocyclic ring selected from the group consisting of 1-indolinyl, morpholino, piperidino, and 1-pyrrolidyl, wherein Z is —CN, —C(O)R$_4$, or —COOR$_4$, R$_4$ is hydrogen or C$_1$–C$_4$ alkyl; and the heterocyclic ring substituents are C$_1$–C$_4$ alkyl or C$_1$–C$_4$ alkoxy; or W may be —OR$_5$ or —N(R$_6$)R$_7$, wherein R$_5$ is hydrogen, C$_1$–C$_4$ alkyl, phenyl, mono C$_1$–C$_4$)alkyl substituted phenyl, mono (C$_1$–C$_4$)alkoxy substituted phenyl, phenyl(C$_1$–C$_2$)alkyl, mono(C$_1$–C$_4$)alkyl substituted phenyl(C$_1$–C$_2$)alkyl, mono (C$_1$–C$_4$)alkoxy substituted phenyl(C$_1$–C$_2$)alkyl, mono (C$_1$–C$_4$)alkoxy(C$_1$–C$_3$)alkyl, or C$_1$–C$_4$ haloalkyl; and R$_6$ and R$_7$ may each be selected from the group consisting of hydrogen, C$_1$–C$_4$ alkyl, C$_5$–C$_7$ cycloalkyl, phenyl and mono- or di-substituted phenyl; each of the phenyl substituents being C$_1$–C$_4$ alkyl or C$_1$–C$_4$ alkoxy and each of the halo groups being fluoro or chloro.

More preferably, R$_3$ is the group, —CH$_2$X, or —C(O)W, wherein X is hydroxy, C$_1$–C$_4$ alkoxy, or C$_2$–C$_4$ acyloxy and W is an unsubstituted or mono-substituted heterocyclic ring selected from the group consisting of 1-indolinyl, morpholino, and piperidino or W is —OR$_5$ wherein R$_5$ is C$_1$–C$_3$ alkyl. Most preferably, R$_3$ is hydroxymethyl, acetoxymethyl, morpholinocarbonyl, piperidinocarbonyl or C$_1$–C$_3$ alkoxycarbonyl.

B and B' in graphic formula I may each be selected from the group consisting of:

(i) the unsubstituted, mono-, di- and tri-substituted aryl groups, phenyl and naphthyl;

(ii) the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in parts (i) and (ii) being selected from the group consisting of hydroxy, aryl, mono(C$_1$–C$_6$) alkoxyaryl, di(C$_1$–C$_6$)alkoxyaryl, mono(C$_1$–C$_6$) alkylaryl, di(C$_1$–C$_6$)alkylaryl, bromoaryl, chloroaryl, fluoroaryl, C$_3$–C$_7$ cycloalkylaryl, C$_3$–C$_7$ cycloalkyl, C$_3$–C$_7$ cycloalkyloxy, C$_3$–C$_7$ cycloalkyloxy(C$_1$–C$_6$) alkyl, C$_3$–C$_7$ cycloalkyloxy(C$_1$–C$_6$)alkoxy, aryl (C$_1$–C$_6$)alkyl, aryl(C$_1$–C$_6$)alkoxy, aryloxy, aryloxy (C$_1$–C$_6$)alkyl, aryloxy(C$_1$–C$_6$)alkoxy, mono- and di(C$_1$–C$_6$)alkylaryl(C$_1$–C$_6$)alkyl, mono- and di(C$_1$–C$_6$) alkoxyaryl(C$_1$–C$_6$)alkyl, mono- and di(C$_1$–C$_6$) alkylaryl(C$_1$–C$_6$)alkoxy, mono- and di(C$_1$–C$_6$) alkoxyaryl(C$_1$–C$_6$)alkoxy, amino, mono(C$_1$–C$_6$) alkylamino, di(C$_1$–C$_6$)alkylamino, diarylamino, N-(C$_1$–C$_6$)alkylpiperazino, N-arylpiperazino, aziridino, indolino, piperidino, arylpiperidino, morpholino, thiomorpholino, tetrahydroquinolino, tetrahydroisoquinolino, pyrryl, C$_1$–C$_6$ alkyl, C$_1$–C$_6$ bromoalkyl, C$_1$–C$_6$ chloroalkyl, C$_1$–C$_6$ fluoroalkyl, C$_1$–C$_6$ alkoxy, mono(C$_1$–C$_6$)alkoxy(C$_1$–C$_4$)alkyl, acryloxy, methacryloxy, bromo, chloro and fluoro;

(iii) the groups represented by the following graphic formulae:

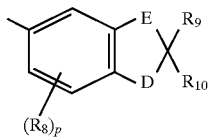

IIA

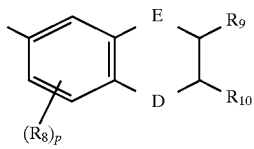

IIB wherein E may be carbon or oxygen and D may be oxygen or substituted nitrogen, provided that when D is substituted nitrogen, E is carbon, said nitrogen substituents being selected from the group consisting of hydrogen, C$_1$–C$_6$ alkyl and C$_2$–C$_6$ acyl; each R$_8$ is C$_1$–C$_6$ alkyl, C$_1$–C$_6$ alkoxy, hydroxy, bromo, chloro or fluoro; R$_9$ and R$_{10}$ are each hydrogen or C$_1$–C$_6$ alkyl; and p is the integer 0, 1 or 2;

(iv) C$_1$–C$_6$ alkyl, C$_1$–C$_6$ bromoalkyl, C$_1$–C$_6$ chloroalkyl, C$_1$–C$_6$ fluoroalkyl, C$_1$–C$_6$ alkoxy(C$_1$–C$_4$)alkyl, C$_3$–C$_6$ cycloalkyl, mono(C$_1$–C$_6$)alkoxy(C$_3$–C$_6$)cycloalkyl, mono(C$_1$–C$_6$)alkyl(C$_3$–C$_6$)cycloalkyl, bromo(C$_3$–C$_6$) cycloalkyl, chloro(C$_3$–C$_6$)cycloalkyl and fluoro (C$_3$–C$_6$)cycloalkyl; and (v) the group represented by the following graphic formula:

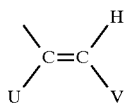

IIC wherein U in graphic formula IIC may be hydrogen or C$_1$–C$_4$ alkyl and V in graphic formula IIC may be selected from the unsubstituted, mono-, and di-substituted members of the group consisting of naphthyl, phenyl, furanyl and thienyl, each of said group substituents in this part (v) being C$_1$–C$_4$ alkyl, C$_1$–C$_4$ alkoxy, bromo, fluoro or chloro; or (vi) B and B' taken together form fluoren-9-ylidene, mono- or di-substituted fluoren-9-ylidene or form a member selected from the group consisting of saturated C$_3$–C$_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene and cyclododecylidene; saturated C$_7$–C$_{12}$, spiro-bicyclic hydrocarbon rings, e.g., bicyclo[2.2.1] heptylidene, i.e., norbornylidene, 1,7,7-trimethyl bicyclo[2.2.1]heptylidene, i.e., bornylidene, bicyclo [3.2.1]octylidene, bicyclo[3.3.1]nonan-9-ylidene and bicyclo[4.3.2]undecane and saturated C$_7$–C$_{12}$ spiro-tricyclic hydrocarbon rings, e.g., tricyclo[2.2.1.0$^{2,6}$] heptylidene and tricyclo[3.3.1.1$^{3,7}$]decylidene, i.e., adamantylidene, and tricyclo[5.3.1.1$^{2,6}$]dodecylidene, said fluoren-9-ylidene substituents being selected from the group consisting of $C_1$–$C_4$ alkyl, $C_1$–$C_4$ alkoxy, bromo, fluoro and chloro.

More preferably, B and B' are each selected from the group consisting of: (i) phenyl, mono-substituted phenyl and di-substituted phenyl, preferably substituted in the meta and/or para positions; (ii) the unsubstituted, mono- and di-substituted heteroaromatic groups furanyl, benzofuran-2-yl, thienyl, benzothien-2-yl, dibenzofuran-2-yl and dibenzothien-2-yl, each of said phenyl and heteroaromatic substituents in (i) and (ii) being selected from the group consisting of hydroxy, aryl, aryloxy, aryl($C_1$–$C_3$)alkyl, amino, mono($C_1$–$C_3$)alkylamino, di($C_1$–$C_3$)alkylamino, N-($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$) alkyl, fluoro and chloro; (iii) the groups represented by the graphic formulae IIA and IIB, wherein E is carbon and D is oxygen, $R_8$ is $C_1$–$C_3$ alkyl or $C_1$–$C_3$ alkoxy, $R_9$ and $R_{10}$ are each hydrogen or $C_1$–$C_4$ alkyl; and p is the integer 0 or 1; (iv) $C_1$–$C_4$ alkyl; and (v) the group represented by the graphic formula IIC wherein U is hydrogen or methyl and V is phenyl or mono-substituted phenyl, said phenyl substituent being selected from the group consisting of $C_1$–$C_3$ alkyl, $C_1$–$C_3$ alkoxy and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

Most preferably, B and B' are each selected from the group consisting of (i) phenyl, mono- and di-substituted phenyl; (ii) the unsubstituted, mono- and di-substituted heteroaromatic groups furanyl, benzofuran-2-yl, thienyl and benzothien-2-yl, each of said phenyl and heteroaromatic substituents in (i) and (ii) being selected from the group consisting of hydroxy, $C_1$–$C_3$ alkyl, $C_1$–$C_3$ alkoxy, aryl, indolino, fluoro and chloro; and (iii) the group represented by graphic formula IIA, wherein E is carbon and D is oxygen, $R_8$ is $C_1$–$C_3$ alkyl or $C_1$–$C_3$ alkoxy, $R_9$ and $R_{10}$ are each hydrogen or $C_1$–$C_3$ alkyl, and p is the integer 0 or 1; or (iv) B and B' taken together form fluoren-9-ylidene, adamantylidene, bornylidene, norbornylidene or bicyclo[3.3.1]nonan-9-ylidene.

Compounds represented by graphic formula I may be prepared by the following described Reactions A through E. Compounds represented by graphic formula V or VA (as shown in Reactions A and B, respectively) are either purchased or prepared by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V or VA in Reaction B. R and R' represent possible substituents, as described hereinbefore with respect to graphic formula I.

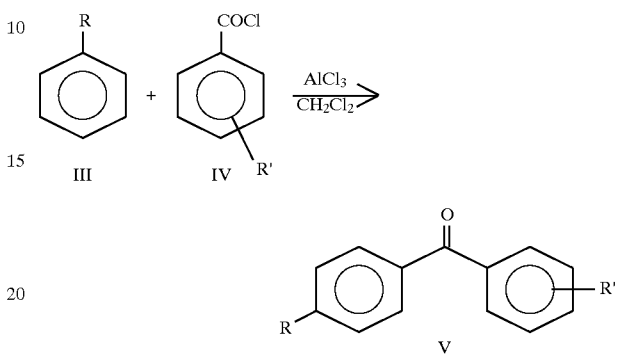

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68.

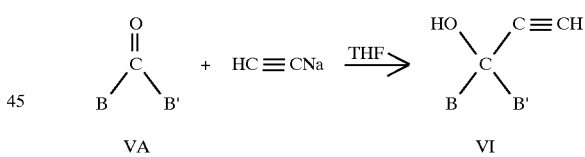

In Reaction C, the fluorene represented by graphic formula VII, which may be purchased, is heated with maleic anhydride (graphic formula VIII). Addition of sodium carbonate to the reaction mixture forms the 9-fluorenylsuccinic acid represented by graphic formula IX. Compound IX is refluxed with acetic anhydride ($Ac_2O$) to form the corresponding anhydride represented by graphic formula X. Compound X is cyclized by heating with salts such as aluminum chloride and sodium chloride to form the 1-carboxy-3-oxo-1,2,3,10b-tetrahydrofluoranthene represented by graphic formula XI. Reaction C is further described in Chem. Abs., Vol. 58, #7882b (1963) and Bergmann et al., "Synthesis of Fluroanthene and its Derivatives", J. Amer. Chem. Soc., Vol. 71, pages 1917–1918 (1949).

Reaction C

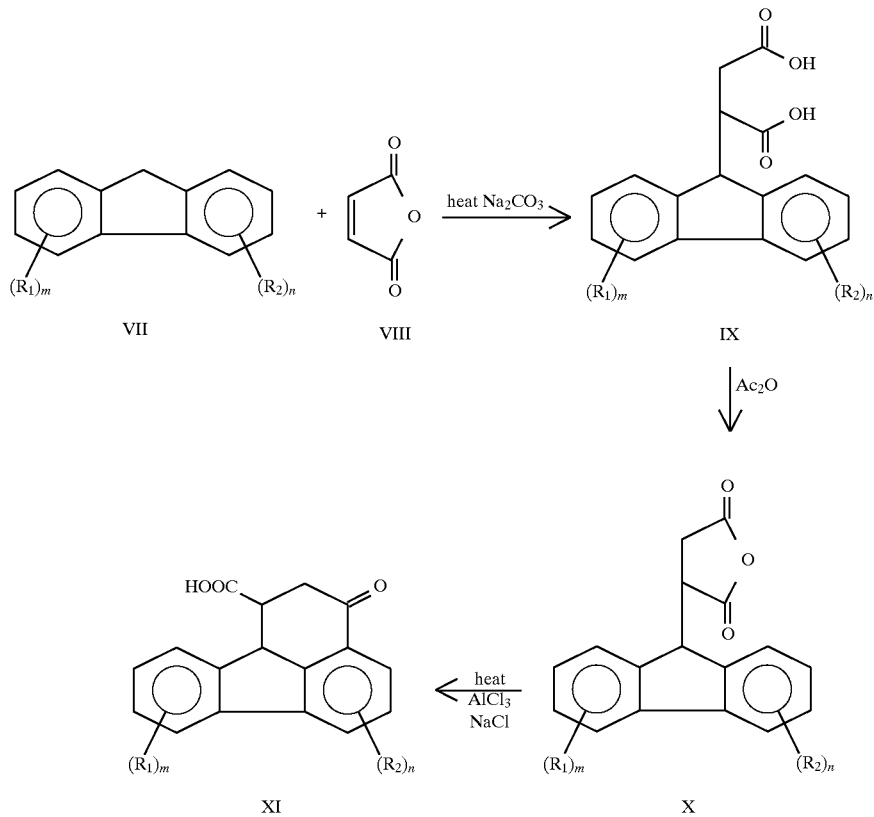

In Reaction D, aromatization of compound XI with potassium hydroxide yields the hydroxy acid represented by graphic formula XII. Alkylation of compound XII with an alcohol such as methanol or ethanol in an acid such as sulfuric acid forms the 1-carboalkoxy-3-hydroxyfluoranthene represented by graphic formula XIII. The 3-hydroxyfluoranthene can also be prepared by the methods described in Journal of Organic Chemistry of USSR, Vol. 5, pages 140–141 (1969) and Angew. Chem. Internat. Edit., Vol. 3, page 587 (1964).

Reaction D

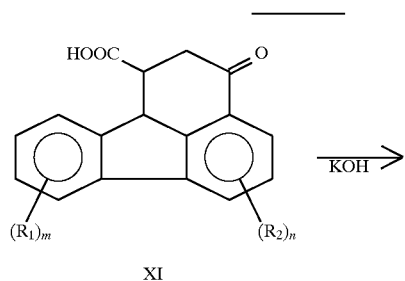

-continued
Reaction D

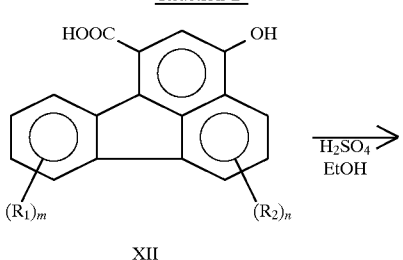

In Reaction E, compound XIII is coupled with the propargyl alcohol represented by graphic formula VI in a suitable solvent such as toluene to form the compounds represented by graphic formula IA. For compounds represented by graphic formula I wherein $R_3$ is other than an alkoxycarbonyl group, compound IA may be derivatized as described in U.S. Pat. No. 5,656,206, column 9, line 18 to column 11, line 50, which disclosure is incorporated herewith in toto by reference.

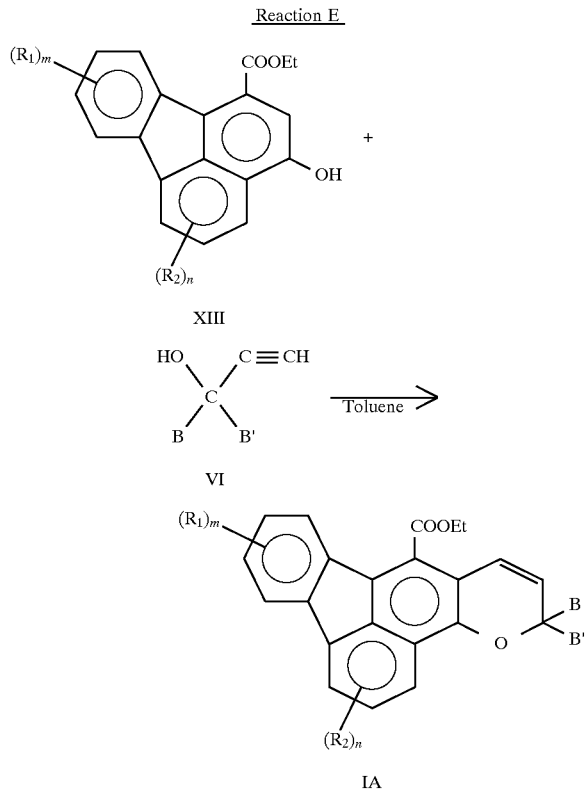

Compounds represented by graphic formulae I and IA may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. The fluoranthenopyrans represented by graphic formula I exhibit activated colors ranging from orange to blue.

Examples of contemplated fluoranthenopyran compounds within the scope of the invention include the following:
(a) 5,5-bis(4-methoxyphenyl)-8-ethoxycarbonyl-5H-fluorantheno[3,2-b]pyran;
(b) 5-(4-methoxyphenyl)-5-(4-morpholinophenyl)-8-ethoxycarbonyl-5H-fluorantheno[3,2-b]pyran;
(c) 5,5-diphenyl-8-ethoxycarbonyl-5H-fluorantheno[3,2-b]pyran;
(d) 5,5-bis(4-methoxyphenyl)-8-methylol-5H-fluorantheno[3,2-b]pyran; and
(e) 5,5-bis(4-methoxyphenyl)-2-methoxy-8-methoxycarbonyl-5H-fluorantheno[3,2-b]pyran.

It is contemplated that the organic photochromic fluoranthenopyrans of the present invention may be used alone, in combination with other fluoranthenopyrans of the present invention, or in combination with one or more other appropriate complementary organic photochromic materials, i.e., organic photochromic compounds having at least one activated absorption maxima within the range of between about 400 and 700 nanometers, or substances containing same, which color when activated to an appropriate hue, and such photochromic compounds/materials may be associated with or incorporated, e.g., dissolved or dispersed, in a polymeric organic host material used to prepare photochromic articles.

Other than where otherwise indicated, all numbers expressing wavelengths, quantities of ingredients or reaction conditions used herein are to be understood as modified in all instances by the term "about".

Examples of complementary organic photochromic compounds include naphthopyrans, chromenes and oxazines; substituted 2H-phenanthro[4,3-b]pyran and 3H-phenanthro [1,2-b]pyran compounds; benzopyran compounds having substituents at the 2-position of the pyran ring including a dibenzo-fused 5 member heterocyclic compound and a substituted or unsubstituted heterocyclic ring, such as a benzothieno or benzofurano ring fused to the benzene portion of the benzopyrans; spiro(benzindoline)naphthopyrans, spiro(indoline)benzopyrans, spiro(indoline)naphthopyrans, spiro(indoline)quinopyrans, spiro(indoline)pyrans, spiro(indoline)napthoxazines, spiro(indoline) pyridobenzoxazines, spiro(benzindoline) pyridobenzoxazines, spiro(benzindoline)naphthoxazines, spiro(indoline)benzoxazines, and mixtures of such photochromic compounds. Many of such photochromic compounds are described in the open literature, e.g., U.S. Pat. Nos. 3,562,172; 3,567,605; 3,578,602; 4,215,010; 4,342, 668; 4,816,584; 4,818,096; 4,826,977; 4,880,667; 4,931, 219; 5,066,818; 5,238,981; 5,274,132; 5,384,077; 5,405, 958; 5,429,774; 5,458,814; 5,466,398; 5,514,817; 5,552, 090; 5,552,091; 5,565,147; 5,573,712; 5,578,252; 5,645,767 and Japanese Patent Publication 62/195383. Spiro(indoline) pyrans are also described in the text, *Techniques in Chemistry,* Volume III, "Photochromism", Chapter 3, Glenn H. Brown, Editor, John Wiley and Sons, Inc., New York, 1971.

Other complementary photochromic substances contemplated are photochromic metal-dithizonates, e.g. mercury dithizonates which are described in, for example, U.S. Pat. No. 3,361,706, fulgides and fulgimides, e.g. the 3-furyl and 3-thienyl fulgides and fulgimides which are described in U.S. Pat. No. 4,931,220 at column 20, line 5 through column 21, line 38.

The disclosures relating to the photochromic compounds found in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., x=X/(X+Y+Z) and y=Y/(X+Y+Z). Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, New York (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to, associated with or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 1.0, e.g., from 0.1 to 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating or film placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

The photochromic compounds of the present invention may be present in an organic solvent or an organic polymeric host. The organic solvent may be selected from the group consisting of benzene, toluene, methyl ethyl ketone, acetone, ethanol, tetrahydrofurfuryl alcohol, N-methyl pyrrolidinone, 2-methoxyethyl ether, xylene, cyclohexane, 3-methyl cyclohexanone, ethyl acetate, tetrahydrofuran, methanol, methyl propinate, ethylene glycol and mixtures thereof. Preferably, the organic solvent is selected from the group consisting of acetone, ethanol, tetrahydrofurfuryl alcohol, 2-methoxyethyl ether, 3-methyl cyclohexanone, N-methyl pyrrolidinone and mixtures thereof.

Preferably, the organic polymeric host material is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials are polymers prepared from individual monomers or mixtures of monomers selected from the following groups:

(a) diacrylate or dimethacrylate compounds represented by graphic formula XIV:

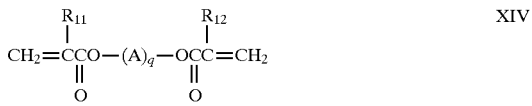

wherein $R_{11}$ and $R_{12}$ may be the same or different and are hydrogen or methyl, A is methylene, i.e., ($CH_2$), and q is an integer of from 1 to 20;

(b) diacrylate or dimethacrylate compounds represented by graphic formula XV:

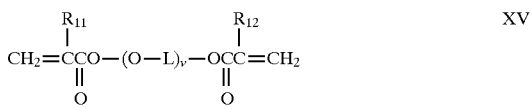

wherein L is $CH_2CR_{12}R_{13}$, $R_{13}$ is hydrogen or methylene and v is an integer of from 1 to 50; and (c) an acrylate or a methacrylate compound having an epoxy group represented by graphic formula XVI:

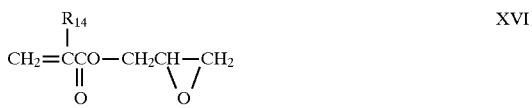

wherein $R_{14}$ is hydrogen or methyl.

In graphic formulae XIV, XV and XVI, like letters used with respect to the definitions of different substituents have the same meaning.

Examples of diacrylate or dimethacrylate compounds represented by graphic formulae XIV and XV include diethylene glycol dimethacrylate, triethylene glycol dimethacrylate, etc., butanediol dimethacrylate and poly(oxyalkylene dimethacrylates), e.g., polyethylene glycol (600) dimethacrylate. Examples of acrylate or methacrylate compounds represented by graphic formula XVI include glycidyl acrylate and glycidyl methacrylate.

Further examples of polymeric organic host materials which may be used with the photochromic compounds described herein include: polymers, i.e., homopolymers and copolymers, of the monomers and mixtures of monomers represented by graphic formulae XIV, XV and XVI, bis(allyl carbonate) monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol polyacrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly(methyl methacrylate), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol(allyl carbonate) monomers, e.g., diethylene glycol bis(allyl carbonate), and acrylate monomers, e.g., ethyl acrylate, butyl acrylate.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly contemplated is use of the photochromic fluoranthenopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the CR-designation, e.g., CR-307 and CR-407.

The present invention is more particularly described in the following examples which are intended as illustrative only, since numerous modifications and variations therein will be apparent to those skilled in the art.

EXAMPLE 1

Step 1

Fluorene (50 grams) and maleic anhydride (30 grams) were mixed in a reaction flask. The resulting mixture was stirred and maintained at 135° C. for six hours. The mixture was cooled to room temperature and a 20 weight percent sodium carbonate solution was slowly added. The resulting mixture was stirred for three hours and then filtered to remove unreacted fluorene. The filtrate was acidified with concentrated hydrochloric acid, filtered, washed and dried. The recovered solid, approximately 25 grams, was used directly in the next step.

Step 2

The product of Step 1 (20 grams) was added to a reaction flask containing acetic anhydride (75 milliliters (mL)) and refluxed for five hours. The resulting reaction mixture was cooled to room temperature and filtered. The filtered solid was washed and dried. The recovered product (42 grams) had a melting point of 168° C. A nuclear magnetic resonance (NMR) spectrum showed the product to have a structure consistent with 9-fluorenylsuccinic anhydride.

Step 3

Aluminum chloride (16 grams) and sodium chloride (10 grams) were placed in a reaction flask and heated up to 130° C. and stirred. The 9-fluorenylsuccinic anhydride from Step 2 (10 grams) was slowly added to the salt mixture and stirred for 10 minutes at 130° C. The reaction mixture was cooled to room temperature and a 20 weight percent solution of hydrochloric acid (50 mL) was added. The reaction mixture was filtered and the recovered solid product was washed and dried, yielding 6 grams. An NMR spectrum showed the product to have a structure consistent with a cis-trans mixture of 1-carboxy-3-oxo-1,2,3,10b-tetrahydrofluoranthene.

Step 4

The 1-carboxy-3-oxo-1,2,3,10b-tetrahydrofluoranthene from Step 3 (5 grams) and potassium hydroxide (7 grams) were added to a reaction flask and melted together at 140° C. for five minutes. The resulting reaction mixture was cooled and water (50 mL) was added. The reaction mixture was acidified with hydrochloric acid and filtered. The recovered solid was washed and dried to yield 3.5 grams of a product having a melting point of 261–262° C. An NMR spectrum showed the product to have a structure consistent with 1-carboxy-3-hydroxy-fluoranthene.

Step 5

The 1-carboxy-3-hydroxy-fluoranthene from Step 4 (2 grams) was added to a reaction flask containing ethanol (20 mL) and concentrated sulfuric acid (2 mL) and refluxed for six hours. The reaction mixture was cooled to room temperature and poured into a beaker containing a mixture of ice and water. The resulting aqueous mixture was extracted with chloroform. The organic layer was separated, washed, dried and concentrated. The concentrate was crystallized from ethyl ether yielding 1.6 grams of the recovered product. An NMR spectrum showed the product to have a structure consistent with 1-ethoxycarbonyl-3-hydroxy-fluoranthene.

Step 6

The 1-ethoxycarbonyl-3-hydroxy-fluoranthene (1.6 grams) from Step 5 was added to a reaction flask containing 2,2-bis(4-methoxyphenyl)propargyl alcohol (2 grams) in toluene (50 mL) and stirred at room temperature. p-Toluene sulfonic acid (100 mL) was added, and the reaction mixture was stirred for eight hours. A 10 weight percent solution of sodium hydroxide (50 mL) was added and the resulting mixture was stirred for one half hour. The organic layer was separated, washed, dried and concentrated. The concentrate was purified on a silica gel column with a 1:1 solvent mixture of chloroform and hexane yielding a recovered product (1.0 gram) having a melting point of 169–170° C. An NMR spectrum showed the product to have a structure consistent with 5,5-bis(4-methoxyphenyl)-8-ethoxycarbonyl-5H-fluorantheno[3,2-b]pyran.

EXAMPLE 2

Part A

Testing was done with the photochromic compound described in Example 1 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold at 60° C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliWatts per square centimeter ($mW/cm^2$). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta OD$) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where % Ta is the percent transmittance in the activated state and the logarithm is to the base 10.

The optical properties of the photochromic compound in the test squares are reported in Table 1. The $\Delta OD/Min$, which represents the sensitivity of the photochromic compound's response to UV light, was measured over the first five (5) seconds of UV exposure, then expressed on a per minute basis. The saturation optical density ($\Delta OD@$ Saturation) was taken under identical conditions as the $\Delta OD/Min$, except UV exposure was continued for 15 minutes. The lambda max (Vis) is the wavelength in nanometers (nm) in the visible spectrum at which the maximum absorption of the activated (colored) form of the photochromic compound in a test square occurs. The lambda max (Vis) wavelength was determined by testing the photochromic test square polymerizate of Part A in a Varian Cary 3 UV-Visible spectrophotometer. The lambda ($\lambda$) max (UV) is the wavelength in nanometers in the ultraviolet range closest to the visible spectrum at which the absorption of the photochromic compound occurs. This absorption was also determined with the same spectrophotometer. The Bleach Rate (T ½) is the time interval in seconds for the absorbance of the activated form of the photochromic compound in the test squares to reach one half the highest absorbance at room temperature (72° F., 22.2° C.) after removal of the source of activating light.

TABLE 1

| | |
|---|---|
| (λ) max (VIS) | 532 nm |
| (λ) max (UV) | 354 nm |
| ΔOD/MIN Sensitivity | 0.55 |
| ΔOD@ Saturation | 0.40 |
| Bleach Rate (T ½) | 44 seconds |

The present invention has been described with reference to specific details of particular embodiments thereof. It is not intended that such details be regarded as limitations upon the scope of the invention except insofar as to the extent that they are included in the accompanying claims.

I claim:

1. A fluoranthenopyran compound represented by the following graphic formula:

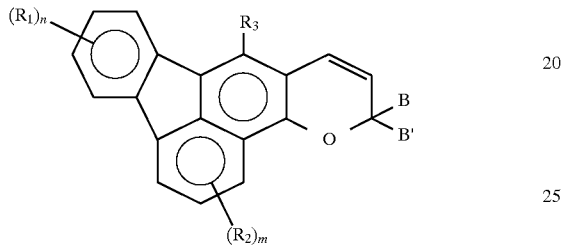

wherein, (a) $R_1$ and $R_2$ are each selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, ($C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro, and m and n are each the integers 0, 1 or 2;

(b) $R_3$ is selected from the group consisting of —$CH_2$X and —C(O)W, wherein X is halogen, hydroxy, benzoyloxy, $C_1$–$C_6$ alkoxy, $C_2$–$C_6$ acyloxy, amino, $C_1$–$C_6$ mono-alkylamino, $C_1$–$C_6$ dialkylamino, morpholino, piperidino, 1-indolinyl, pyrrolidyl, trimethylsilyloxy, or the group, —OCH($R_4$)Z, W is the group, —OCH($R_4$)Z, or an unsubstituted, mono-substituted, or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl, wherein Z is —CN, —$CF_3$, halogen, —C(O)$R_4$, or —COO$R_4$, $R_4$ is hydrogen or $C_1$–$C_6$ alkyl; said heterocyclic ring substituents being selected from $C_1$–$C_6$ alkyl and $C_1$–$C_6$ alkoxy; or W is —O$R_5$ or —N($R_6$)$R_7$, wherein $R_5$ is selected from the group consisting of hydrogen, allyl, $C_1$–$C_6$ alkyl, phenyl, mono($C_1$–$C_6$) alkyl substituted phenyl, mono($C_1$–$C_6$)alkoxy-substituted phenyl, phenyl($C_1$–$C_3$)alkyl, mono($C_1$–$C_6$) alkyl substituted phenyl($C_1$–$C_3$)alkyl, mono($C_1$–$C_6$) alkoxy substituted phenyl($C_1$–$C_3$)alkyl, mono($C_1$–$C_6$) alkoxy($C_1$–$C_4$)alkyl, and $C_1$–$C_6$ haloalkyl; and $R_6$ and $R_7$ are each selected from the group consisting of hydrogen, $C_1$–$C_6$ alkyl, $C_5$–$C_7$ cycloalkyl, phenyl and mono- or di-substituted phenyl; each of said phenyl substituents being $C_1$–$C_6$ alkyl or $C_1$–$C_6$ alkoxy; and each of said halogen or halo groups being fluoro or chloro; and (c) B and B' are each selected from the group consisting of:

(i) the unsubstituted, mono-, di- and tri-substituted aryl groups, phenyl and naphthyl;

(ii) the unsubstituted, mono- and di-substituted heteroaromatic groups furanyl, benzofuran-2-yl, benzofuran-3-yl, thienyl, benzothien-2-yl, benzothien-3-yl, dibenzofuranyl, dibenzothienyl, and fluorenyl, each of said aryl and heteroaromatic substituents in (c)(i) and (ii) being selected from the group consisting of aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$) alkyl, $C_3$–$C_7$ cycloalkyloxy($C_1$–$C_6$)alkoxy, aryl ($C_1$–$C_6$)alkyl, aryl($C_1$–$C_6$)alkoxy, aryloxy, aryloxy ($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono ($C_1$–$C_6$)alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$) alkoxy($C_1$–$C_6$)alkyl, acryloxy, methacryloxy, bromo, chloro and fluoro;

(iii) the groups represented by the following graphic formulae:

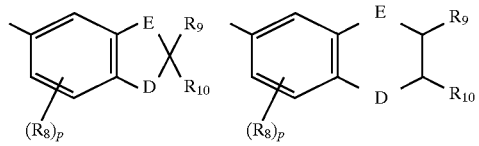

wherein E is carbon or oxygen and D is oxygen or substituted nitrogen, provided that when D is substituted nitrogen, E is carbon, said nitrogen substituents being selected from the group consisting of hydrogen, $C_1$–$C_6$ alkyl and $C_2$–$C_6$ acyl; each $R_8$ is $C_1$–$C_6$ alkyl, $C_1$–$C_6$ alkoxy, hydroxy, bromo, chloro or fluoro; $R_9$ and $R_{10}$ are each hydrogen or $C_1$–$C_6$ alkyl; and p is the integer 0, or 2;

(iv) $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy ($C_1$–$C_4$)alkyl, $C_3$–$C_6$cycloalkyl, mono($C_1$–$C_6$) alkoxy($C_3$–$C_6$)cycloalkyl, mono($C_1$–$C_6$)alkyl ($C_3$–$C_6$)-cycloalkyl, bromo($C_3$–$C_6$)cycloalkyl, chloro($C_3$–$C_6$)cycloalkyl and fluoro($C_3$–$C_6$) cycloalkyl; and (v) the group represented by the following graphic formula:

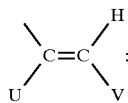

IIC wherein U is hydrogen or $C_1$–$C_4$ alkyl and V is selected from the unsubstituted, mono-, and di-substituted members of the group consisting of naphthyl, phenyl, furanyl and thienyl, each of said group substituents being $C_1$–$C_4$ alkyl, $C_1$–$C_4$ alkoxy, bromo, fluoro or chloro; or (vi) B and B' taken together form fluoren-9-ylidene, mono- or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, bromo, fluoro and chloro.

2. The fluoranthenopyran of claim 1 wherein:

(a) $R_1$ and $R_2$ are each selected from the group consisting of $C_1$–$C_4$ alkyl, $C_1$–$C_4$ alkoxy, chloro and fluoro, and m and n are each 0 or 1;

(b) $R_3$ is selected from the group consisting of —$CH_2X$ and —$C(O)W$, wherein X is hydroxy, $C_1$–$C_4$ alkoxy, or $C_2$–$C_4$ acyloxy, W is the group, —$OCH(R_4)Z$, or an unsubstituted or mono-substituted heterocyclic ring selected from the group consisting of 1-indolinyl, morpholino, piperidino, and 1-pyrrolidyl, wherein Z is —CN, —$C(O)R_4$, or —$COOR_4$, $R_4$ is hydrogen or $C_1$–$C_4$ alkyl; said heterocyclic ring substituents being selected from $C_1$–$C_4$ alkyl and $C_1$–$C_4$ alkoxy; or W is —$OR_5$ or —$N(R_6)R_7$, wherein $R_5$ is selected from the group consisting of hydrogen, $C_1$–$C_4$ alkyl, phenyl, mono($C_1$–$C_4$)alkyl substituted phenyl, mono($C_1$–$C_4$) alkoxy substituted phenyl, phenyl($C_1$–$C_2$)alkyl, mono ($C_1$–$C_4$)alkyl substituted phenyl($C_1$–$C_2$)alkyl, mono ($C_1$–$C_4$)alkoxy substituted phenyl($C_1$–$C_2$)alkyl, mono ($C_1$–$C_4$)alkoxy($C_1$–$C_3$)alkyl, and $C_1$–$C_4$ haloalkyl; and $R_6$ and $R_7$ are each selected from the group consisting of hydrogen, $C_1$–$C_4$ alkyl, $C_5$–$C_7$ cycloalkyl, phenyl and mono- or di-substituted phenyl; each of said phenyl substituents being $C_1$–$C_4$ alkyl or $C_1$–$C_4$ alkoxy; and each of said halo groups being fluoro or chloro;

(c) B and B' are each selected from the group consisting of:

(i) phenyl, mono-substituted phenyl and di-substituted phenyl;

(ii) the unsubstituted, mono-substituted and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (c) (i) and (ii) being selected from the group consisting of hydroxy, aryl, aryloxy, aryl($C_1$–$C_3$)alkyl, amino, mono($C_1$–$C_3$)alkylamino, di($C_1$–$C_3$)alkylamino, N-($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$) alkoxy($C_1$–$C_3$)alkyl, fluoro and chloro;

(iii) the groups represented by the following graphic formulae:

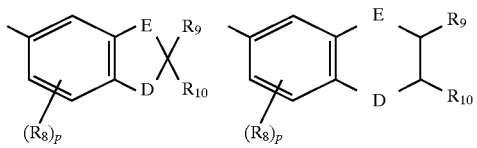

wherein E is carbon and D is oxygen, $R_8$ is $C_1$–$C_3$ alkyl or $C_1$–$C_3$ alkoxy, $R_9$ and $R_{10}$ are each hydrogen or $C_1$–$C_4$ alkyl; and p is the integer 0 or 1;

(iv) $C_1$–$C_4$ alkyl; and (v) the group represented by the following graphic formula:

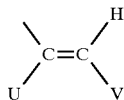

wherein U is hydrogen or methyl and V is phenyl or mono-substituted phenyl, said phenyl substituent being selected from the group consisting of $C_1$–$C_3$ alkyl, $C_1$–$C_3$ alkoxy and fluoro; or (vi) B and B' taken together form a fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

3. The fluoranthenopyran of claim 2 wherein:

(a) $R_1$ and $R_2$ are each $C_1$–$C_3$ alkyl or $C_1$–$C_3$ alkoxy, and m and n are each the integers 0 or 1;

(b) $R_3$ is selected from the group consisting of —$CH_2X$ and —$C(O)W$, wherein X is hydroxy, $C_1$–$C_4$ alkoxy, or $C_2$–$C_4$ acyloxy and W is an unsubstituted or mono-substituted heterocyclic ring selected from the group consisting of 1-indolinyl, morpholino, and piperidino; or W is —$OR_5$ wherein $R_5$ is $C_1$–$C_3$ alkyl; and (c) B and B' are each selected from the group consisting of:

(i) phenyl, mono-substituted and di-substituted phenyl;

(ii) the unsubstituted, mono-, and di-substituted heteroaromatic groups furanyl, benzofuran-2-yl, thienyl and benzothien-2-yl, each of said phenyl and heteroaromatic substituents in (c) (i) and (ii) being selected from the group consisting of hydroxy, $C_1$–$C_3$ alkyl, $C_1$–$C_3$ alkoxy, aryl, indolino, fluoro and chloro; and (iii) the group represented by the following graphic formula:

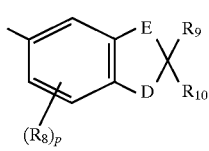

wherein E is carbon and D is oxygen, $R_8$ is $C_1$–$C_3$ alkyl or $C_1$–$C_3$ alkoxy, $R_9$ and $R_{10}$ are each hydrogen or $C_1$–$C_3$ alkyl, and p is the integer 0 or 1; or (iv) B and B' taken together form fluoren-9-ylidene, adamantylidene, bornylidene, norbornylidene or bicyclo(3.3.1)nonan-9-ylidene.

4. The naphthopyran of claim 3 wherein $R_3$ is hydroxymethyl, acetoxymethyl, morpholinocarbonyl, piperidinocarbonyl or $C_1$–$C_3$ alkoxycarbonyl; and B and B' are each phenyl, methoxy substituted phenyl, morpholino substituted phenyl, dibenzofuran-2-yl, or 2,3-dihydrobenzofuran-5-yl.

5. A fluoranthenopyran compound selected from the group consisting of:
   (a) 5,5-bis(4-methoxyphenyl)-8-ethoxycarbonyl-5H-fluorantheno[3,2-b]pyran;
   (b) 5-(4-methoxyphenyl)-5-(4-morpholinophenyl)-8-ethoxycarbonyl-5H-fluorantheno[3,2-b]pyran;
   (c) 5,5-diphenyl-8-ethoxycarbonyl-5H-fluorantheno[3,2-b]pyran;
   (d) 5,5-bis(4-methoxyphenyl)-8-methylol-5H-fluorantheno[3,2-b]pyran; and
   (e) 5,5-bis(4-methoxyphenyl)-2-methoxy-8-methoxycarbonyl-5H-fluorantheno[3,2-b]pyran.

6. A photochromic article comprising a polymeric organic host material and a photochromic amount of the fluoranthenopyran compound of claim 1.

7. The photochromic article of claim 6 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylatemonomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

8. The photochromic article of claim 7 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

9. The photochromic article of claim 8 wherein the photochromic compound is present in an amount of from 0.05 to 1.0 milligram per square centimeter of organic host material surface to which the photochromic substance(s) is incorporated or applied.

10. The photochromic article of claim 9 wherein said transparent polymer is an optical element.

11. The photochromic article of claim 10 wherein said optical element is a lens.

12. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the fluoranthenopyran compound of claim 4.

13. A photochromic article comprising a polymerizate of an optical organic resin monomer and a photochromic amount of the fluoranthenopyran compound of claim 1.

14. The photochromic article of claim 13 wherein the refractive index of the polymerizate is from about 1.48 to about 1.75.

15. The photochromic article of claim 14 wherein the refractive index of the polymerizate is from about 1.495 to about 1.66.

16. A photochromic article comprising, in combination, a solid transparent polymeric organic host material, and a photochromic amount of each of (a) at least one fluoranthenopyran compound of claim 1, and (b) at least one other organic photochromic compound having at least one activated absorption maxima within the range of between about 400 and 700 nanometers.

17. The photochromic article of claim 16 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

18. The photochromic article of claim 17 wherein the polymeric organic host material is a solid transparent homopolymer or copolymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

19. The photochromic article of claim 16 wherein the organic photochromic compound (b) is selected from the group consisting of naphthopyrans, chromenes, oxazines, metal-dithizonates, fulgides and fulgimides.

20. The photochromic article of claim 19 wherein the total amount of photochromic compound present is from 0.05 to 1.0 milligram per square centimeter of organic host material surface to which the photochromic substance(s) is incorporated or applied.

21. The photochromic article of claim 19 wherein said transparent polymeric organic host material is an optical element.

22. The photochromic article of claim 21 wherein said optical element is a lens.

23. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of each of (a) at least one fluoranthenopyran compound of claim 4, and (b) at least one other organic photochromic compound having at least one activated absorption maxima within the range of between about 400 and 700 nanometers.

* * * * *